United States Patent
Felt et al.

(10) Patent No.: US 11,222,166 B2
(45) Date of Patent: Jan. 11, 2022

(54) ITERATIVELY EXPANDING CONCEPTS

(71) Applicant: International Business Machines Corporation, Armonk, NY (US)

(72) Inventors: Paul Lewis Felt, Springville, UT (US); Brendan Bull, Durham, NC (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

(21) Appl. No.: 16/687,843

(22) Filed: Nov. 19, 2019

(65) Prior Publication Data

US 2021/0149990 A1    May 20, 2021

(51) Int. Cl.
| | |
|---|---|
| *G06F 40/169* | (2020.01) |
| *G06F 40/242* | (2020.01) |
| *G06F 40/247* | (2020.01) |
| *G06F 40/205* | (2020.01) |

(52) U.S. Cl.
CPC ......... *G06F 40/169* (2020.01); *G06F 40/242* (2020.01); *G06F 40/247* (2020.01); *G06F 40/205* (2020.01)

(58) Field of Classification Search
CPC ...... G06F 16/3331; G06F 16/36; G06F 19/32; G06F 19/321; G06F 40/205; G06F 40/253; G06F 40/279; G06F 40/30; G06F 40/169; G06F 40/20; G06F 40/247; G06F 40/242
See application file for complete search history.

(56) References Cited

U.S. PATENT DOCUMENTS

| | | | | |
|---|---|---|---|---|
| 6,366,683 B1 * | 4/2002 | Langlotz | ............... | G16H 15/00 382/128 |
| 7,233,891 B2 * | 6/2007 | Bond | ................... | G06F 40/211 704/9 |
| 7,610,192 B1 * | 10/2009 | Jamieson | ............... | G16H 15/00 704/9 |
| 8,086,468 B2 * | 12/2011 | Kim | .................... | G06Q 10/067 705/2 |

(Continued)

FOREIGN PATENT DOCUMENTS

| | | |
|---|---|---|
| CN | 106875014 A | 6/2017 |
| CN | 108537240 A | 9/2018 |

OTHER PUBLICATIONS

Hliaoutakis, A., Zervanou, K., & Petrakis, E. G. (2009). The AMTEx approach in the medical document indexing and retrieval application. Data & Knowledge Engineering, 68(3), 380-392.

(Continued)

*Primary Examiner* — Wilson W Tsui
(74) *Attorney, Agent, or Firm* — Cantor Colburn LLP; Ryan Lewis

(57) ABSTRACT

Aspects of the invention include a method for iteratively expanding concepts. The method includes building a set of expressions extracted from an ontology to form a cache, the set of expressions based at least in part on respective target concepts. Receiving a document and performing a first traversal of the document to identify first surface forms related to the respective target concepts. Performing a second traversal of the document to identify second surface forms that modify the first surface forms. Annotating the document by comparing the modifying surface forms to target concepts and the set of expressions in the cache.

17 Claims, 6 Drawing Sheets

(56) References Cited

U.S. PATENT DOCUMENTS

| | | | | |
|---|---|---|---|---|
| 8,429,179 B1 * | 4/2013 | Mirhaji | ............... | G06F 16/2465 |
| | | | | 707/756 |
| 8,793,199 B2 * | 7/2014 | Syeda-Mahmood | ... | G06F 19/00 |
| | | | | 706/12 |
| 9,524,289 B2 * | 12/2016 | Rachevsky | ............. | G06F 40/30 |
| 9,594,747 B2 | 3/2017 | Kim et al. | | |
| 2004/0024720 A1 * | 2/2004 | Fairweather | ............ | G06F 8/427 |
| | | | | 706/46 |
| 2005/0004891 A1 | 1/2005 | Mahoney et al. | | |
| 2005/0240439 A1 * | 10/2005 | Covit | .................... | G06Q 10/10 |
| | | | | 705/2 |
| 2009/0070103 A1 * | 3/2009 | Beggelman | ............. | G06F 40/20 |
| | | | | 704/9 |
| 2010/0063799 A1 * | 3/2010 | Jamieson | ................ | G06F 16/36 |
| | | | | 704/9 |
| 2014/0046934 A1 * | 2/2014 | Zhou | ................. | G06F 16/24526 |
| | | | | 707/723 |
| 2014/0149407 A1 * | 5/2014 | Qian | ...................... | G16H 30/40 |
| | | | | 707/737 |
| 2014/0181128 A1 * | 6/2014 | Riskin | ................. | G06F 16/3344 |
| | | | | 707/756 |
| 2016/0055162 A1 | 2/2016 | Woolf | | |
| 2016/0299975 A1 | 10/2016 | Acar et al. | | |
| 2019/0102697 A1 * | 4/2019 | Casalonga | .............. | G06F 40/00 |
| 2019/0311807 A1 * | 10/2019 | Kannan | .................... | G06N 5/04 |

OTHER PUBLICATIONS

Jiménez-Ruiz, E. & Grau, B. C. (Oct. 2011). Logmap: Logic-based and scalable ontology matching. In International Semantic Web Conference, 273-288. Springer, Berlin, Heidelberg.

Anonymous (May 2009). Process For Prototyping, Refining or Validating Medical Image Processing Algorithms Based On Extracting And Mapping of Image Attributes. IPCOM000182842D.pp. 1-10.

* cited by examiner

ITERATIVELY EXPANDING CONCEPTS

BACKGROUND

The present invention generally relates to concept matching, and more specifically, to iteratively expanding concepts.

Source data annotation is a process of labeling unstructured data to make it usable for downstream processing. Annotating or labeling data organizes unstructured data to make the data more understandable to computer-based processes. Furthermore, annotation is an important aspect of the improvement of computer model performance. Data annotation highlights the important words, texts, or objects of source data by using the annotation techniques and makes source data more recognizable to computer systems.

SUMMARY

Embodiments of the present invention are directed to iteratively expanding concepts. A non-limiting example computer-implemented method includes building a set of expressions extracted from an ontology to form a cache, the set of expressions based at least in part on respective target concepts. Receiving a document and performing a first traversal of the document to identify first surface forms related to the respective target concepts. Performing a second traversal of the document to identify second surface forms that modify the first surface forms. Annotating the document by comparing the modifying surface forms to target concepts and the set of expressions in the cache.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
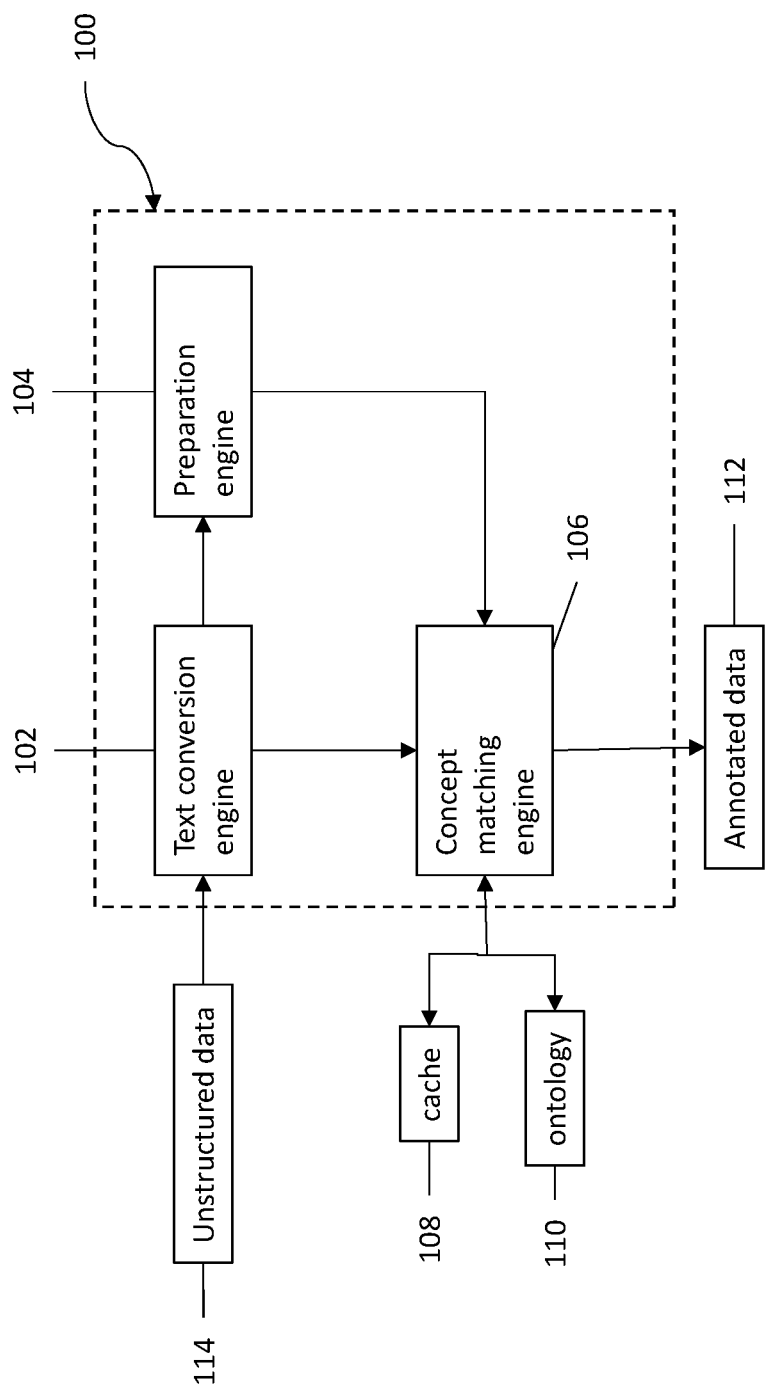
FIG. 1 depicts a system for iterative expanded concept matching according to embodiments of the present invention.

The diagrams depicted herein are illustrative. There can be many variations to the diagrams, or the operations described therein without departing from the spirit of the invention. For instance, the actions can be performed in a differing order or actions can be added, deleted or modified. Also, the term "coupled" and variations thereof describe having a communications path between two elements and does not imply a direct connection between the elements with no intervening elements/connections between them. All of these variations are considered a part of the specification.

DETAILED DESCRIPTION

One or more embodiments of the present invention provide an annotation system that iteratively traverses a document to first identify surface forms related to target concepts. The system then performs a second and, if necessary, a subsequent traversal to identify any surface forms that modify the initially identified surface forms. The system then annotates the document based on the modifying surface forms.

The amount of structured and unstructured data stored and available for analysis continues to increase rapidly. The ability of data scientists, companies, and individuals to access and analyze large quantities of electronic data sources for intelligent decision making is a key element to success in modern society. Structured data is typically stored in large data warehouses, and several tools exist to enable parsing and analysis of the data. Furthermore, a growing interest in the medical field has developed for accessing and analyzing unstructured data for intelligent decision making related to patient care. Unstructured data includes word processing documents, e-mail, web pages, text files, electronic medical records (EMRs), images, and audio and video streams.

To process unstructured documents, engineers employ natural language processing techniques to analyze the unstructured text documents and match certain concepts to textual expressions or "surface forms", found in the unstructured documents. These textual expressions are sometimes referred to as surface forms. Concept matching techniques primarily rely on dictionaries for matching concepts to the surface forms. For example, in the medical space, a concept detection technique may match a concept with a unique concept identification (CUI) from a medical-based ontology.

However, current concept matching techniques rely on a one-pass system. In other words, the conventional concept matching engines perform a single pass over a text in an unstructured document and attempt to identifying relations among smaller, more atomic concepts based on the single pass. Empirical data suggests that the single-pass approach is not sufficient to match a user's needs. Conventional single-pass concept matching methods attempts to discover concepts in text that don't match existing surface forms. However, a single pass by a conventional context analyzer is insufficient, as illustrated for the below referenced exemplary two lines of text.

"How much does it cost to get the bags under my eyes removed?"

"I tore a ligament in my left knee and elbow"

In the first sentence, the user is asking about a procedure for periorbital edema removal. However, it's expressed as a composition of two concepts, one of which a single pass context analyzer could not retrieve from the Unified Medical Language System (UMLS). "Bags under my eyes" is not a dictionary form that can resolve to "periorbital edema" unless an expanded concept matching is applied. But even that doesn't fully capture what the user is asking. Combining "periorbital edema" with "removed" via the iterative expanded concept matching mechanism "periorbital edema removed" puts the context analyzer in a position to match the proper concepts.

Similarly, conventional concept matching for "tore a ligament" returns the basic "ruptured ligament" concept, but the user is clearly searching for a ligament in the left knee and elbow. To properly identify the concept, the context analyzer needs to look for a torn ligament concept in relation to the appropriate body parts.

The following example is provided for illustrative purposes. Take, for example, the phrase "I broke my collarbone" being examined in a single-pass system. Upon receiving the phrase, the system searches for annotations/words of interests, also referred to as targets. Targets can be concepts as well as words found in text. In this example, the word "collarbone" is the target. Next the single-pass system searches for a modifier of "collarbone", which in this case would be "broke". Using this target/modifier pair, the single-pass system searches a cache for a match.

The cache can be built offline and, for example, maps medical concepts (CUIs) to cached target/modifier pairs. In this example, the cache includes cached target/modifier pairs that have been mapped to concepts. In this instance, the cached pair of "clavicle/fracture" has been mapped to CUI C0159658, the concept for "fracture of clavicle". The single-pass system takes the derived target/modifier pair (collarbone/broke) and begins to search the cache for a synonymous target, in this case "clavicle" is synonymous with "collarbone". The single-pass system then searches each cached clavicle/modifier pair for a modifier that is synonymous with "broken". In this case, "fracture" is synonymous with "broken". The single-pass system identifies the cached target/modifier pair of "clavicle/fracture" and matches the mapped concept, CUI C0159658.

However, due to the system only using a single pass, text such as "I tore a ligament in my knee" may return concepts for "tore a ligament" or "ligament in my knee", but the correct concept for "torn knee ligament" would not be identified. In the instances of medical document annotation, this could result in returning a medical code for torn ligament as opposed to a medical code for torn knee ligament. Using an iterative approach, the iterative-pass system determines whether a modifier modifies "tore a ligament", which in this case is "knee". The iterative-pass system, then searches the cache for a match to the concept "torn ligament" as the target and knee as the modifier.

One or more embodiments of the present invention address one or more of the above-described shortcomings of the prior art by providing a system that augments expanded matching techniques by iterating each term until convergence. Initially, the system executes an expanded concept matching program and look for any expanded concepts in the textual expression. A natural language process (NLP) model then performs a second or subsequent pass to re-analyze the phrase for any modifiers of the terms. The system then retrieves the proper concept from a desired ontology, for example, the UMLS.

Turning now to FIG. 1, a block diagram of a system 100 to annotate an unstructured span of text or unstructured data, is generally shown in accordance with one or more embodiments of the present invention. The system 100 includes a text conversion engine 102, a preparation engine 104, and a concept matching engine 106. The system is in operable communication with a cache 108 and an ontology 110, which can include multiple dictionaries. A receiver (not shown) of the text conversion engine 102 receives a document, a portion of which includes unstructured data 114 from a data source (not shown). A document can be in any form, for example, PDF, DOC, HTML, etc. The text conversion module 102 converts the document into plain text.

The text conversion engine 102 transmits the converted document to the preparation engine 104 and the concept matching engine 106, which includes multiple annotators. The preparation engine 104 retrieves information pertaining to a model(s), for the concept matching engine 106 (not shown) from a server, for example, a cloud computing server. A model includes a list of attributes that describe an entity, while a dictionary provides a list of all possible values for an attribute. The preparation engine 104 queries the server system to extract the definitions of a group of desired concepts for data mining an ontology 108. The preparation engine 104 may further use any existing structured and unstructured data to obtain rules and models to assist with concept matching from the converted document. The preparation engine 104 also obtains a set of target semantic types that contain triggers for the concepts that are of interest to the data mining.

The preparation engine 104 transmits/shares the desired concepts, models, dictionaries, and learned rules and models to concept matching engine 106. The concept matching engine 106 receives and applies the desired concepts, respective dictionaries, learned rules, and models to use for extracting information from the ontology 108. The concept matching engine 106 performs multiple passes of the document. Based on the extracted terms from the document, the concept matching engine 106 maps the desired target concepts and semantic types in the document to concepts from a dictionary, for example, the UMLS.

The concept matching engine 106 is operable to receive an unstructured or structured document. Upon receipt, the concept matching engine 106 uses basic dictionary matching, to identify semantic types in base surface forms found in the document. Then, the concept matching engine 106 uses the learned rules to find modifiers that describe the target. However, given the variations of variations in expressing the same concept, concept matching engine 106 may not identify each concept precisely on a first pass. Therefore, the concept matching engine 106 employs natural language processing techniques to perform a second pass to search for any modifies of terms and modifiers obtained from the first pass. Based on the results of the second pass, concept matching engine 106, concepts identified as relating to the target. The concept matching engine 106, then stores this information in the cache 106. A target can have multiple modifiers that map to the concepts stored in the cache 106. The concept matching engine 106 annotates the document to produce annotated data 112, based on the mapping stored in cache 108.

The concept matching engine 106 is equipped with artificial intelligence circuitry to employ one or more artificial intelligence models to assist with the annotation generation. The artificial intelligence models include, but are not limited to decision trees, decision tables, support vector machines, clustering models, hidden Markov models, and Gaussian mixture models. An artificial intelligence model is trained using a training set compiled of structured text, unstructured text, and annotations.

In embodiments of the invention, the concept matching engine 106 can also be implemented as so-called classifiers (described in more detail below). In one or more embodiments of the invention, the features described herein can be implemented on the processing system 600 shown in FIG. 6, or can be implemented on a neural network (not shown). In embodiments of the invention, the features of the concept matching engine 106 can be implemented by configuring and arranging the processing system 600 to execute machine learning (ML) algorithms. In general, ML algorithms, in effect, extract features from received data (e.g., inputs to the concept matching engine 106) in order to "classify" the received data. Examples of suitable classifiers include, but are not limited to, neural networks (described in greater detail below), support vector machines (SVMs), logistic regression, decision trees, hidden Markov Models (HMMs), etc. The end result of the classifier's operations, i.e., the "classification," is to predict a class for the data. The ML algorithms apply machine learning techniques to the received data in order to, over time, create/train/update a unique "model." The learning or training performed by the concept matching engine 106 can be supervised, unsupervised, or a hybrid that includes aspects of supervised and unsupervised learning. Supervised learning is when training data is already available and classified/labeled. Unsupervised learning is when training data is not classified/labeled so it must be developed through iterations of the classifier. Unsupervised learning can utilize additional learning/training methods including, for example, clustering, anomaly detection, neural networks, deep learning, and the like.

In embodiments of the invention where the concept matching engine 106 are implemented as neural networks, a resistive switching device (RSD) can be used as a connection (synapse) between a pre-neuron and a post-neuron, thus representing the connection weight in the form of device resistance. Neuromorphic systems are interconnected processor elements that act as simulated "neurons" and exchange "messages" between each other in the form of electronic signals. Similar to the so-called "plasticity" of synaptic neurotransmitter connections that carry messages between biological neurons, the connections in neuromorphic systems such as neural networks carry electronic messages between simulated neurons, which are provided with numeric weights that correspond to the strength or weakness of a given connection. The weights can be adjusted and tuned based on experience, making neuromorphic systems adaptive to inputs and capable of learning. For example, a neuromorphic/neural network for handwriting recognition is defined by a set of input neurons, which can be activated by the pixels of an input image. After being weighted and transformed by a function determined by the network's designer, the activations of these input neurons are then passed to other downstream neurons, which are often referred to as "hidden" neurons. This process is repeated until an output neuron is activated. Thus, the activated output neuron determines (or "learns") which character was read. Multiple pre-neurons and post-neurons can be connected through an array of RSD, which naturally expresses a fully-connected neural network. In the descriptions here, any functionality ascribed to the system 100 can be implemented using the processing system 600 applies.

The concept matching engine 106 can perform the first pass and the second pass. NLP analysis techniques on the unstructured data/documents 114 as well as the ontology 110 for the second pass. NLP is utilized subsequent to the first pass to derive modifiers of the surface forms identified in the first pass. The concept matching engine 106 can analyze the unstructured data/documents 114 by parsing, syntactical analysis, morphological analysis, and other processes including, statistical modeling and statistical analysis. The type of NLP analysis can vary by language and other considerations. The NLP analysis is utilized to generate a set of NLP structures and/or features which modify the previously identified structures and/or features from the first pass.

These additional NLP structures include a translation and/or interpretation of the natural language input, including synonymous, antonyms, and variants thereof. The concept matching engine 106 can analyze the additional structural features to determine a context for the originally identified structures and features. NLP analysis can be utilized to extract attributes (features) from the natural language. These extracted attributes can be analyzed by the concept matching engine 106 to determine one or more annotations.

Figure 2:
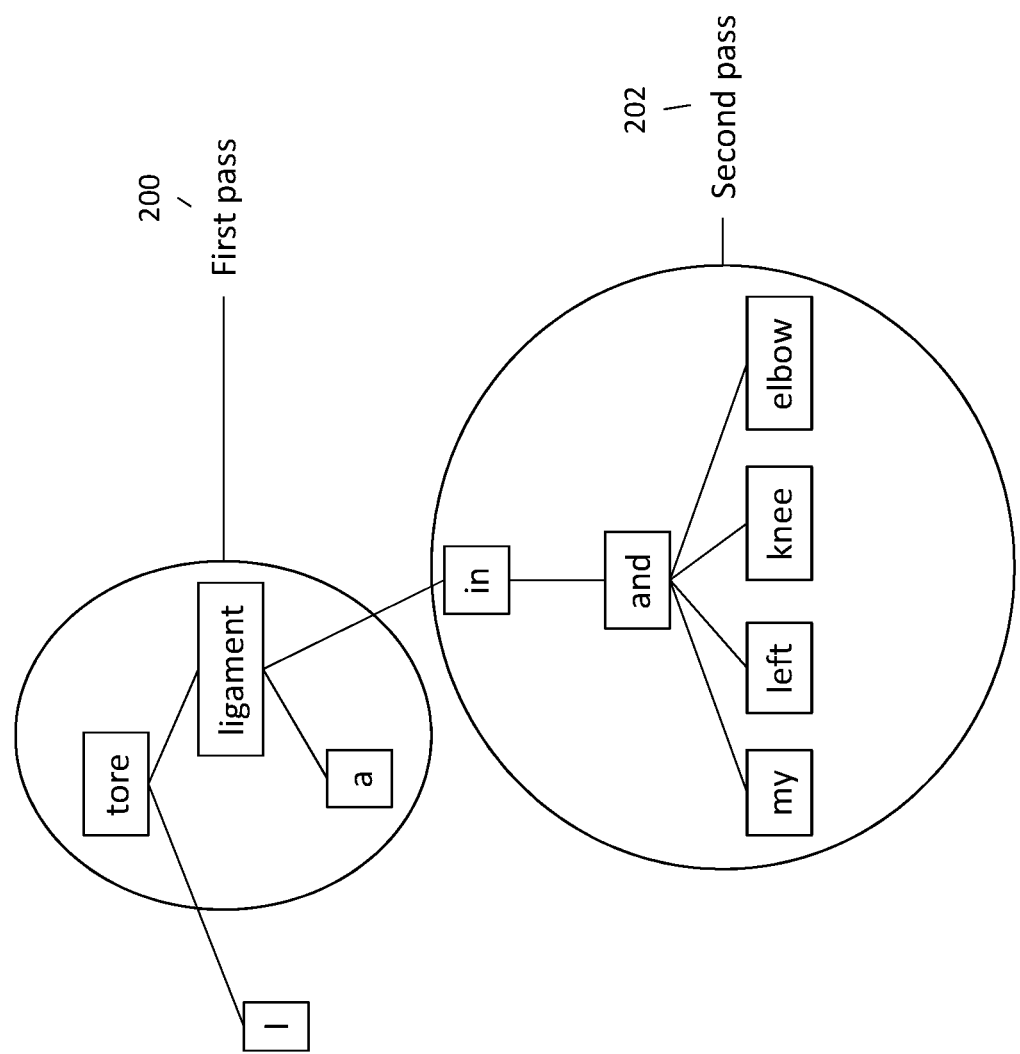
FIG. 2 depicts the results of an illustrative parse tree according to one or more embodiments of the present invention.

Referring to FIG. 2, an illustration of iterative expanded concept matching is shown. The phrase "I tore a ligament in my left knee and elbow" is provided as an example. Initially, the system executes an expanded concept matching program by performing a first pass 200 to look for any expanded concepts in the phrase. In this case, the first pass 200 identifies the terms "tore" "ligament, and "a" and identifies the concept UMLS CUI C0262538 ("Ligament rupture"). However, this first pass 200 fails to identify the body part of the ligament.

A natural language process (NLP) model is employed to perform a second pass 202 to re-analyze the phrase for any modifiers of the terms. As seen in this example, the second pass or subsequent pass 202 reveals the modifiers "left", "knee", and "elbow". The second or subsequent pass 202 reveals the body parts that have torn ligaments and properly identify the concepts that the user is looking for. The system can now retrieve the proper concept from the UMLS.

Figure 3:
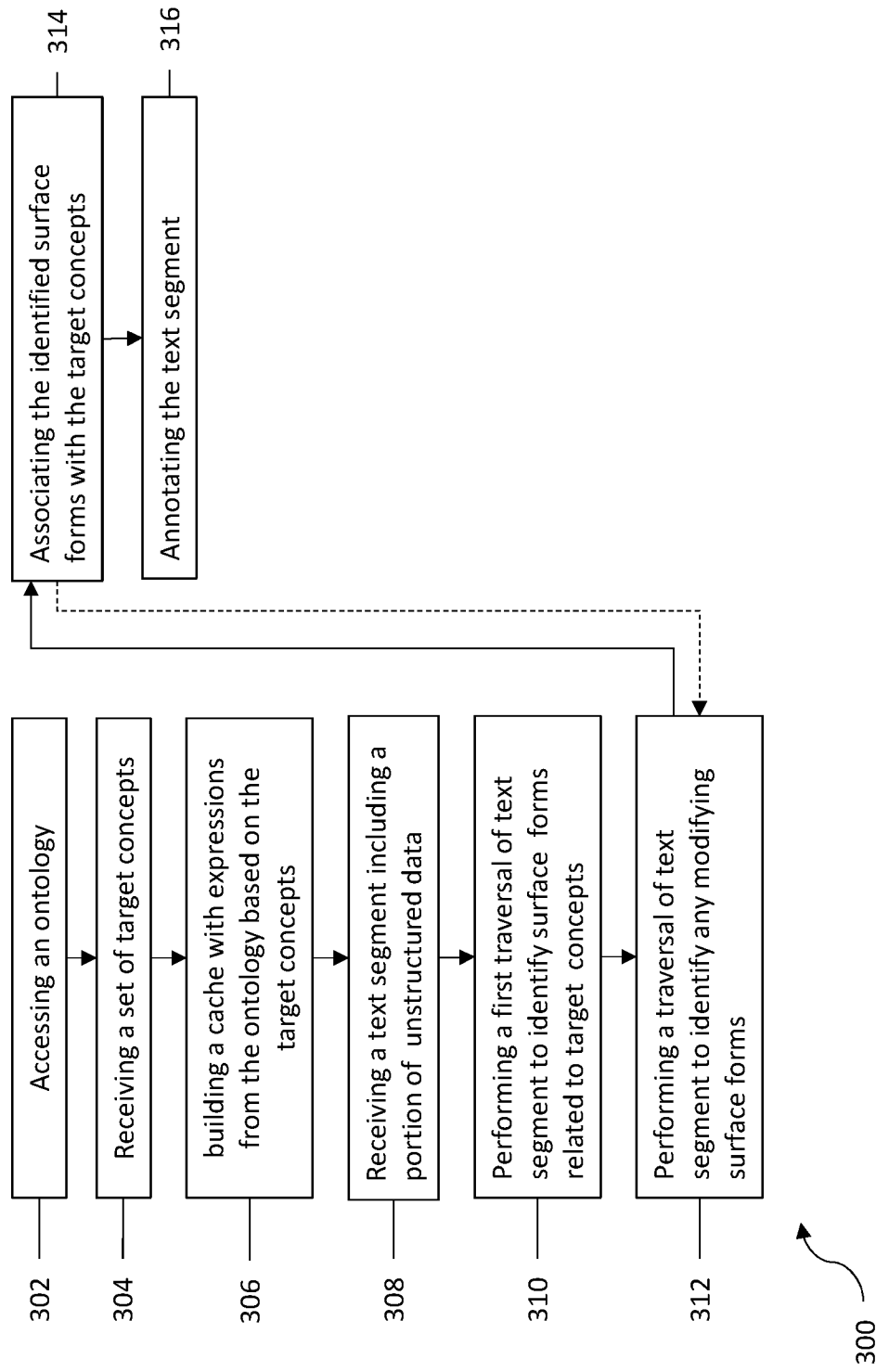
FIG. 3 depicts a flow diagram of a method for expanded iterative concept matching according to one or more embodiments of the present invention.

Referring to FIG. 3 a flow diagram of a method 300 for expanded iterative concept matching according to one or more embodiments of the present invention, is shown. The method 300 includes receiving an ontology at block 302, for example a dictionary including the UMLS or other medical-based dictionary. At block 304, the method 300 includes determining a set of target concepts. The target concepts are determined based on what concepts are of interest, for example medical-based applications, diagnosis, health care administration; medical coding, etc. At block 306, includes parsing the ontology to build a cache of a set of expressions for each target concept. At block 308 includes receiving a text segment from a document that includes a portion of unstructured data. At block 310, the method 300 includes traversing the document for a first pass to identify text related to the target concepts. For example, as illustrated in FIG. 2 the first pass reveals a verb "tore" and an object of the verb, "ligament". After performing the first pass, the method 300, further includes traversing the document text to perform a second pass at block 312, as illustrated by the dashed line. The second pass includes using natural language techniques to identify any modifying terms. As seen in FIG. 2, the second pass reveals the left knee and elbow, which describe the body parts with torn ligaments. At block 314, the method 300 includes associating the identified language in the text segment with any target concepts. At block 316, the method 300 includes annotating the text segment from the document by comparing the set of target concepts to the set of expressions in the cache.

Additional processes may also be included. It should be understood that the processes depicted in FIG. 3 represent illustrations, and that other processes may be added or existing processes may be removed, modified, or rearranged without departing from the scope and spirit of the present invention.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is a service oriented with a focus on statelessness, low coupling, modularity, and semantic interoperability. At the heart of cloud computing is an infrastructure that includes a network of interconnected nodes.

Figure 4:
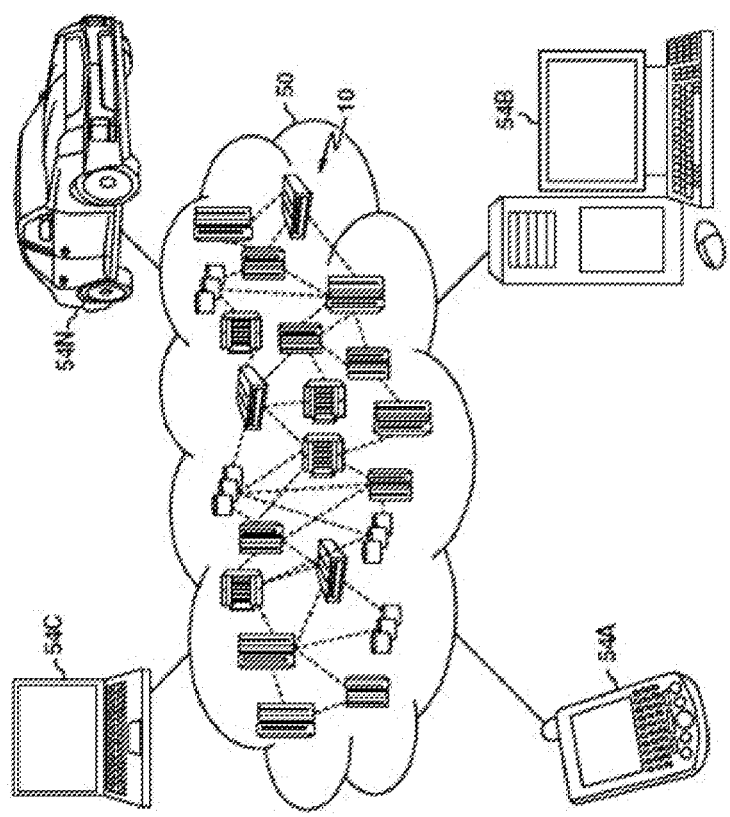
FIG. 4 depicts a cloud computing environment according to one or more embodiments of the present invention.

Referring now to FIG. 4, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
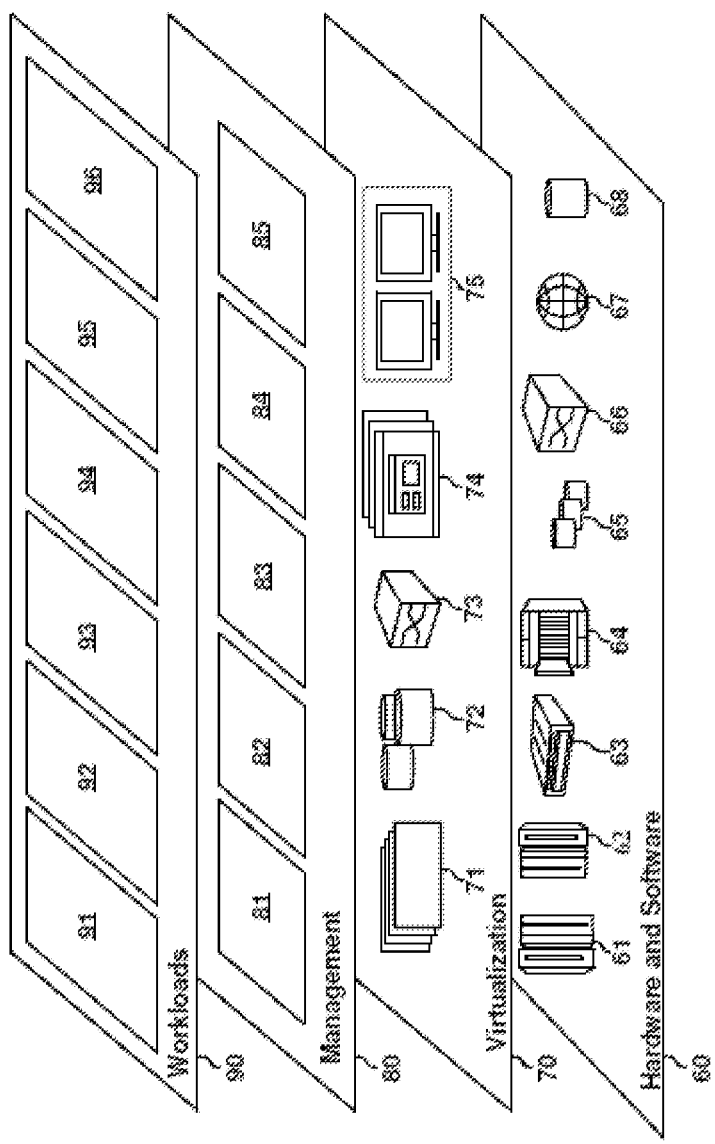
FIG. 5 depicts abstraction model layers according to one or more embodiments of the present invention.

Referring now to FIG. 5, a set of functional abstraction layers provided by cloud computing environment 50 (FIG. 1) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and expanded concept matching 96.

Figure 6:
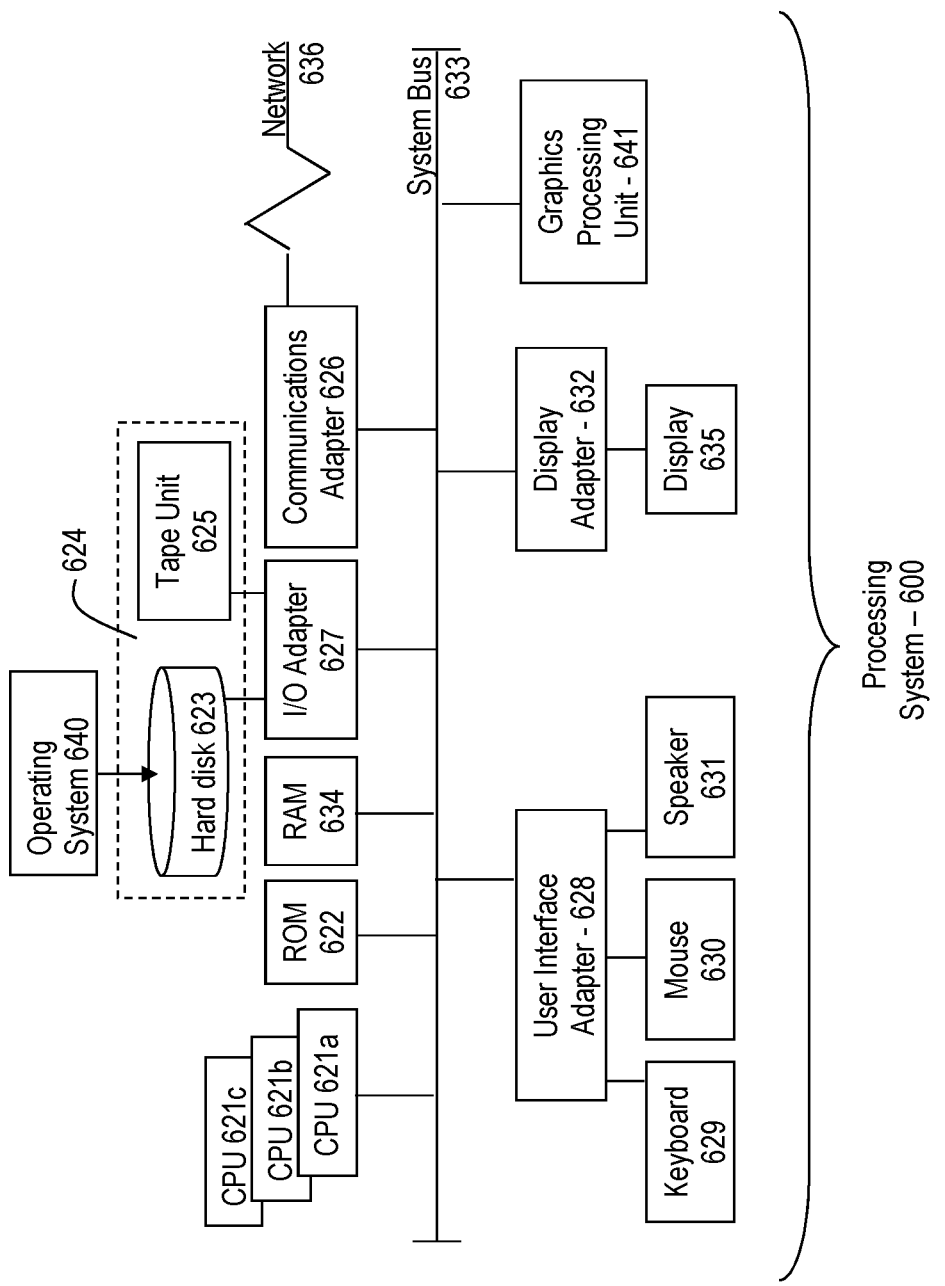
FIG. 6 depicts a block diagram of a computer system for use in implementing one or more embodiments of the present invention.

Referring to FIG. 6, there is shown an embodiment of a processing system 600 for implementing the teachings herein. In this embodiment, the system 600 has one or more central processing units (processors) 621a, 621b, 621c, etc. (collectively or generically referred to as processor(s) 621). In one or more embodiments, each processor 621 may include a reduced instruction set computer (RISC) microprocessor. Processors 621 are coupled to system memory 634 and various other components via a system bus 633. Read only memory (ROM) 622 is coupled to the system bus 633 and may include a basic input/output system (BIOS), which controls certain basic functions of system 600.

FIG. 6 further depicts an input/output (I/O) adapter 627 and a network adapter 626 coupled to the system bus 6633. I/O adapter 27 may be a small computer system interface (SCSI) adapter that communicates with a hard disk 623 and/or tape storage drive 625 or any other similar component. I/O adapter 627, hard disk 623, and tape storage device 625 are collectively referred to herein as mass storage 624. Operating system 40 for execution on the processing system 600 may be stored in mass storage 624. A network adapter 626 interconnects bus 633 with an outside network 636 enabling data processing system 600 to communicate with other such systems. A screen (e.g., a display monitor) 635 is connected to system bus 633 by display adaptor 632, which may include a graphics adapter to improve the performance of graphics intensive applications and a video controller. In one embodiment, adapters 627, 626, and 632 may be connected to one or more I/O busses that are connected to system bus 633 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 633 via user interface adapter 628 and display adapter 632. A keyboard 629, mouse 630, and speaker 631 all interconnected to bus 633 via user interface adapter 628, which may include, for example, a Super I/O chip integrating multiple device adapters into a single integrated circuit.

In exemplary embodiments, the processing system 600 includes a graphics processing unit 641. Graphics processing unit 641 is a specialized electronic circuit designed to manipulate and alter memory to accelerate the creation of images in a frame buffer intended for output to a display. In general, graphics processing unit 641 is very efficient at manipulating computer graphics and image processing and has a highly parallel structure that makes it more effective than general-purpose CPUs for algorithms where processing of large blocks of data is done in parallel.

Thus, as configured in FIG. 6, the system 600 includes processing capability in the form of processors 621, storage capability including system memory 634 and mass storage 6624, input means such as keyboard 629 and mouse 630, and output capability including speaker 31 and display 635. In one embodiment, a portion of system memory 634 and mass storage 624 collectively store an operating system which coordinates the functions of the various components shown in FIG. 6.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
   determining a set of target concepts;
   parsing an ontology to build a cache of a set of expressions for each target concept of the set of target concepts, wherein each expression from the set of expressions maps a paired particular concept and particular modifier to a specific medical concept;
   receiving a document comprising a text segment that includes unstructured data;
   performing, by a concept matching engine comprising a neural network, a first traversal of the text segment of the document to identify first surface forms, the first surface forms comprising a target object term and a verb term that modifies the target object term, wherein the neural network comprises a plurality of resistive switching devices which each encode a weight of an element of a natural language process (NLP) model of the neural network;
   iteratively performing, by the concept matching engine, one or more additional traversals of the text segment to identify one or more second surface forms that modify the identified first surface forms, wherein at least one of the one or more second surface forms comprises a body part term that modifies the target object term of the verb term, and wherein the body part term is absent from the first surface form;
   identifying a first target concept using the set of expressions based upon the target object term and the verb term;
   identifying at least one second target concept using the set of expressions based upon the target object term and the body part term; and
   annotating the text segment of the document with an annotation by providing to the neural network the first target concept as the particular concept and the body part term as the particular modifier to search the cache to identify the specific medical concept, wherein the neural network is trained on structured text, unstructured text, and annotations, and wherein the annotation to the text segment comprises the identified specific medical concept.

2. The computer-implemented method of claim 1, wherein performing the one or more additional traversals comprises analyzing the document via a natural language processing technique.

3. The computer-implemented method of claim 1, further comprising mapping the set of target concepts to expressions found in the ontology.

4. The computer-implemented method of claim 1, wherein each respective surface form of the first surface forms is a synonym, antonym, or variant of a target concept.

5. The computer-implemented method of claim 1, wherein the ontology comprises a dictionary.

6. The computer-implemented method of claim 1, wherein the document comprises unstructured text.

7. A system comprising:
   a memory having computer readable instructions; and
   one or more processors for executing the computer readable instructions, the computer readable instructions controlling the one or more processors to perform operations comprising:
   determining a set of target concepts;
   parsing an ontology to build a cache of a set of expressions for each target concept of the set of target concepts, wherein each expression from the set of expressions maps a paired particular concept and particular modifier to a specific medical concept;
   receiving a document comprising a text segment that includes unstructured data;
   performing, by a concept matching engine comprising a neural network, a first traversal of the text segment of the document to identify first surface forms, the first surface forms comprising a target object term and a verb term that modifies the target object term, wherein the neural network comprises a plurality of resistive switching devices which each encode a weight of an element of a natural language process (NLP) model of the neural network;
   iteratively performing, by the concept matching engine, one or more additional traversals of the text segment to identify one or more second surface forms that modify the identified first surface forms, wherein at least one of the one or more second surface forms comprises a body part term that modifies the target object term of the verb term, and wherein the body part term is absent from the first surface form;
   identifying a first target concept using the set of expressions based upon the target object term and the verb term;

identifying at least one second target concept using the set of expressions based upon the target object term and the body part term; and annotating the text segment of the document with an annotation by providing to the neural network the first target concept as the particular concept and the body part term as the particular modifier to search the cache to identify the specific medical concept, wherein the neural network is trained on structured text, unstructured text, and annotations, and wherein the annotation to the text segment comprises the identified specific medical concept.

8. The system of claim 7, wherein performing the one or more additional traversals comprises analyzing the document via a natural language processing technique.

9. The system of claim 7, further comprising mapping the set of target concepts to expressions found in the ontology.

10. The system of claim 7, wherein each respective surface form of the first surface forms is a synonym, antonym, or variant of a target concept.

11. The system of claim 7, wherein the ontology comprises a dictionary.

12. The system of claim 7, wherein the document comprises unstructured text.

13. A computer program product comprising a computer readable storage medium having program instructions embodied therewith, the program instructions executable by a processor to cause the processor to perform operations comprising:

determining a set of target concepts;

parsing an ontology to build a cache of a set of expressions for each target concept of the set of target concepts, wherein each expression from the set of expressions maps a paired particular concept and particular modifier to a specific medical concept;

receiving a document comprising a text segment that includes unstructured data;

performing, by a concept matching engine comprising a neural network, a first traversal of the text segment of the document to identify first surface forms, the first surface forms comprising a target object term and a verb term that modifies the target object term, wherein the neural network comprises a plurality of resistive switching devices which each encode a weight of an element of a natural language process (NLP) model of the neural network;

iteratively performing, by the concept matching engine, one or more additional traversals of the text segment to identify one or more second surface forms that modify the identified first surface forms, wherein at least one of the one or more second surface forms comprises a body part term that modifies the target object term of the verb term, and wherein the body part term is absent from the first surface form;

identifying a first target concept using the set of expressions based upon the target object term and the verb term;

identifying at least one second target concept using the set of expressions based upon the target object term and the body part term; and annotating the text segment of the document with an annotation by providing to the neural network the first target concept as the particular concept and the body part term as the particular modifier to search the cache to identify the specific medical concept, wherein the neural network is trained on structured text, unstructured text, and annotations, and wherein the annotation to the text segment comprises the identified specific medical concept.

14. The computer program product of claim 13, wherein performing the one or more additional traversals comprises analyzing the document via a natural language processing technique.

15. The computer program product of claim 13, further comprising mapping the set of target concepts to expressions found in the ontology.

16. The computer program product of claim 13, wherein each respective surface form of the first surface forms is a synonym, antonym, or variant of a target concept.

17. The computer program product of claim 13, wherein the ontology comprises a dictionary.

* * * * *